United States Patent
Sundquist et al.

(10) Patent No.: US 6,934,589 B2
(45) Date of Patent: Aug. 23, 2005

(54) SYSTEM AND METHOD FOR PLACING ENDOCARDIAL LEADS

(75) Inventors: Stephen Sundquist, Minnetonka, MN (US); Arnold Thornton, Roseville, MN (US); Roger Dahl, Andover, MN (US); Duane Zytkovicz, Ham Lake, MN (US); Kenneth C. Gardeski, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 253 days.

(21) Appl. No.: 09/827,108

(22) Filed: Apr. 5, 2001

(65) Prior Publication Data

US 2002/0147487 A1 Oct. 10, 2002

Related U.S. Application Data

(60) Provisional application No. 60/259,054, filed on Dec. 29, 2000.

(51) Int. Cl.[7] .............................................. A61N 1/00
(52) U.S. Cl. ..................................... 607/122; 607/126
(58) Field of Search ............................... 607/116–128; 604/96.01, 103.04

(56) References Cited

U.S. PATENT DOCUMENTS

| 4,506,680 A | 3/1985 | Stokes ........................ 128/786 |
| 4,577,642 A | 3/1986 | Stokes ........................ 128/784 |
| 4,606,118 A | 8/1986 | Cannon et al. ............... 29/825 |
| 4,711,251 A | 12/1987 | Stokes ........................ 128/784 |
| 4,808,164 A | 2/1989 | Hess ........................... 604/95 |

(Continued)

FOREIGN PATENT DOCUMENTS

WO      9832375      7/1998      ............ A61B/5/04

OTHER PUBLICATIONS

Product sheet, Apex Medical Technologies, Inc., "New Development Synthetic Polyisoprene Dip Molded Medical Device Components" (Jan. 12, 2001).
Product sheet, Bracco Diagnostics, "Isovue" (Feb. 27, 2001).
Term paper, Riordan, Madeline, "Iopamidol" (Oct. 22, 1998).

(Continued)

*Primary Examiner*—Mark Bockelman
(74) *Attorney, Agent, or Firm*—Daniel G. Chapik; Girma Wolde-Michael

(57) ABSTRACT

An improved system and method for deploying medical electrical leads is disclosed. The system includes a guiding device such as a guidewire used to navigate the vascular system of a body. The guiding device includes a fixation member that can be deployed to maintain the guiding device at a desired location within the vascular system. The fixation member may be an inflatable device such as a balloon, or alternatively, may be an expandable device constructed of flexible fibers that has both an expanded and a contracted state. The system may further include a coupling member located adjacent to the guiding device. The coupling member may be a rail extending distally from a proximal end of the guiding device to a point proximal the fixation member. In an alternative embodiment of the invention, the coupling member is a channel included in the body of the guiding device adapted to slidably engage an electrode assembly. The coupling member is adapted to allow the electrode assembly to be slid to the distal end of the coupling member and deployed at a predetermined implant site. In one embodiment of the invention, the coupling member is movable with respect to the guiding device. This allows the coupling member to be re-positioned to multiple implant sites to deploy more than one electrode while the fixation mechanism remains stationary within a patient's vascular system. According to yet another aspect of the invention, the guiding device includes a lumen to delivery fluoro visible medium.

18 Claims, 17 Drawing Sheets

U.S. PATENT DOCUMENTS

| | | | |
|---|---|---|---|
| 5,003,990 A | 4/1991 | Osypka | 128/772 |
| 5,014,696 A | 5/1991 | Mehra | 128/419 D |
| 5,067,489 A | 11/1991 | Lind | 128/772 |
| 5,071,407 A | 12/1991 | Termin et al. | 604/104 |
| 5,099,838 A | 3/1992 | Bardy | 128/419 D |
| 5,246,014 A | 9/1993 | Williams et al. | 607/122 |
| 5,304,218 A | 4/1994 | Alferness | 607/122 |
| 5,381,790 A | 1/1995 | Kanesaka | 128/642 |
| 5,383,853 A | 1/1995 | Jung et al. | 604/96 |
| 5,415,639 A * | 5/1995 | VandenEinde et al. | 604/528 |
| 5,458,621 A | 10/1995 | White et al. | 607/5 |
| 5,545,204 A | 8/1996 | Cammilli et al. | 607/123 |
| 5,687,723 A | 11/1997 | Avitall | 128/642 |
| 5,704,908 A * | 1/1998 | Hofmann et al. | 604/21 |
| 5,746,701 A | 5/1998 | Noone | 600/585 |
| 5,755,765 A | 5/1998 | Hyde et al. | 607/122 |
| 5,803,928 A | 9/1998 | Tockman et al. | 607/122 |
| 5,833,694 A | 11/1998 | Poncet | 606/108 |
| 5,851,226 A | 12/1998 | Skubitz et al. | 607/126 |
| 5,902,331 A | 5/1999 | Bonner et al. | 607/122 |
| 5,916,178 A | 6/1999 | Noone et al. | 600/585 |
| 6,006,137 A | 12/1999 | Williams | 607/119 |
| 6,129,749 A | 10/2000 | Bartig et al. | 607/122 |
| 6,132,456 A * | 10/2000 | Sommer et al. | 607/127 |
| 6,165,140 A | 12/2000 | Ferrera | 600/585 |
| 6,179,851 B1 | 1/2001 | Barbut et al. | 606/159 |
| 6,527,769 B2 * | 3/2003 | Langberg et al. | 606/41 |
| 6,697,677 B2 * | 2/2004 | Dahl et al. | 607/128 |

OTHER PUBLICATIONS

Brochure, FlexMedics, "FlexFinder Guidewires—A complete selection of high performance guidewires for vascular and non–vascular applications" (1996).

Loctite Medical Product Selector Guide (Dec. 1994).

Application Case History, Loctite, "Loctite Instant Adhesive Improves Quality in Catheter Assembly" (1996).

Brochure, Raychem Corporation Medical Products, Tinel Superelastic Alloys, "Superelastic materials and components for advanced medical instruments and devices" (Feb. 1993).

Product Sheet, Cook Inc., "Roadrunner PC Wire Guides" (Jan. 12, 2001).

NiTi Smart Sheet, Shape Memory Applications, Inc., "Comparison of Properties of NiTi and Stainless Steel" (Jan. 7, 1997).

* cited by examiner

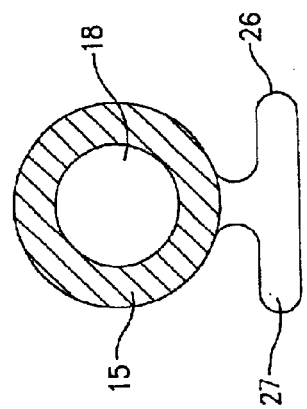
FIG. IE
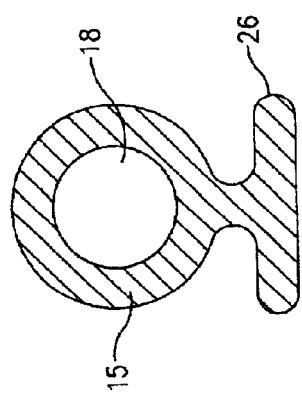
FIG. ID
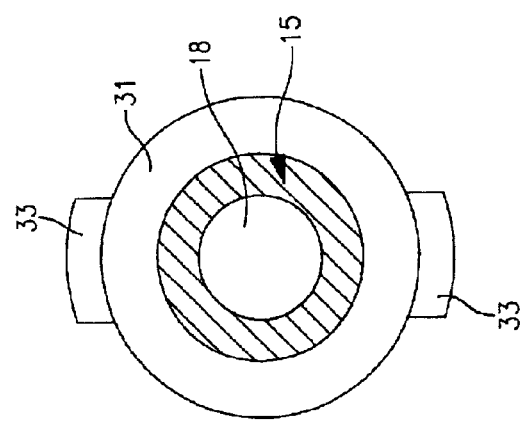
FIG. IC

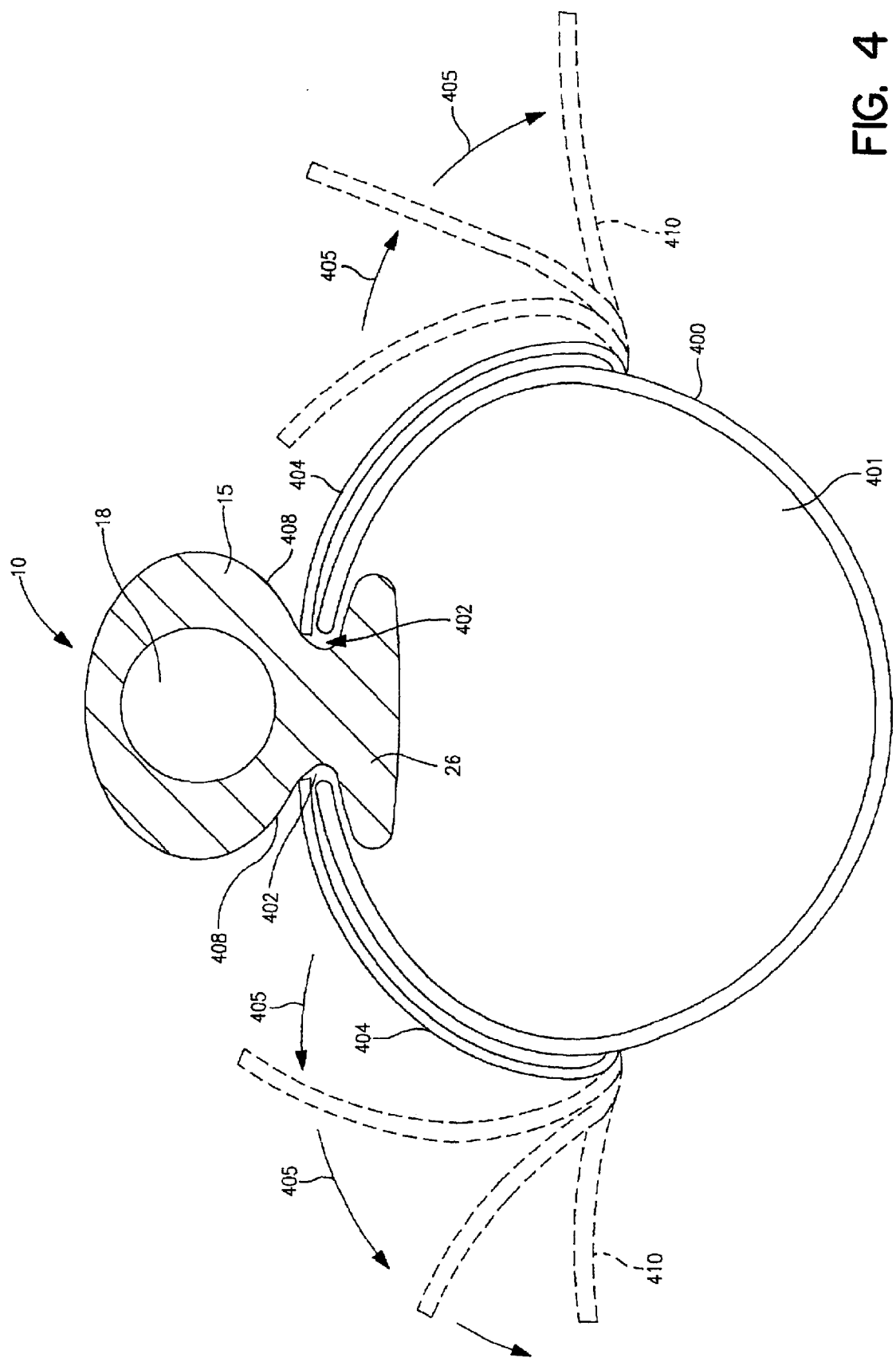

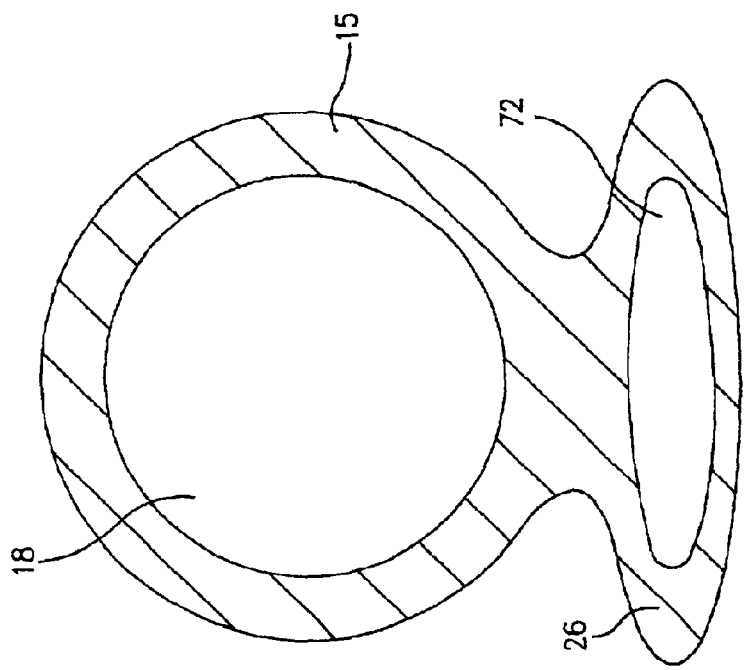
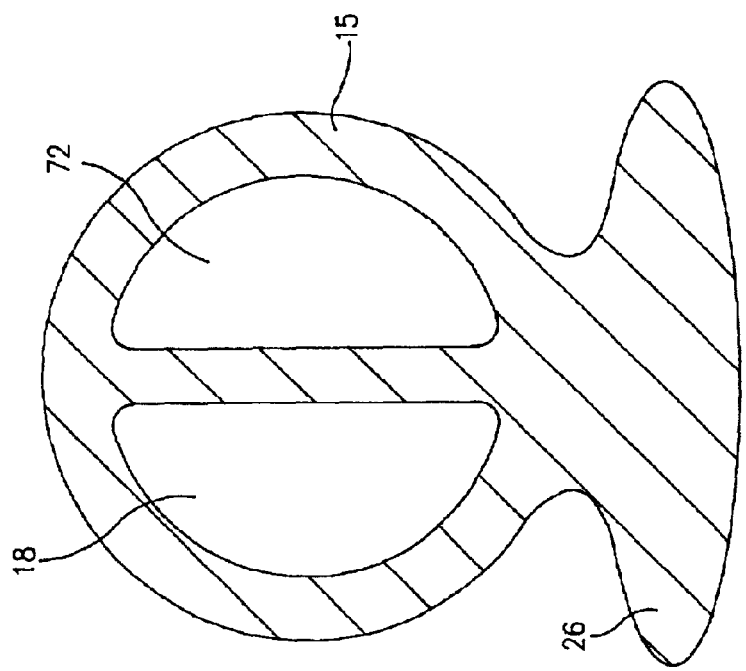

SYSTEM AND METHOD FOR PLACING ENDOCARDIAL LEADS

RELATED APPLICATIONS

This Application claims priority to provisionally-filed U.S. Patent Application Ser. No. 60/259,054 filed Dec. 29, 2000 entitled "System and Method for Placing Endocardial Leads", which is incorporated herein by reference in its entirety.

FIELD OF THE INVENTION

The present invention relates generally to a system and method for placing one or more implantable cardiac leads within a coronary artery or cardiac vein; and more particularly, relates to using a guidewire to deploy one or more endocardial leads, wherein the guidewire includes a fixation means to retain the desired site of implant during the deployment process.

BACKGROUND OF THE INVENTION

Implantable medical electrical stimulation and/or sensing leads are well known in the fields of cardiac stimulation and monitoring, including cardiac pacing and cardioversion/defibrillation. In the field of cardiac stimulation and monitoring, endocardial leads are placed through a transvenous route to locate one or more sensing and/or stimulation electrodes along, or at the distal end of, the lead in a desired location within a heart chamber or interconnecting vasculature. In order to achieve reliable sensing of the cardiac electrogram and/or to apply stimulation that effectively paces or cardioverts the heart chamber, it is necessary to accurately position the electrode surface against the endocardium or within the myocardium at the desired site and fix it during an acute post-operative phase until fibrous tissue growth occurs.

The pacemaker or defibrillator implantable pulse generator (IPG) or the monitor is typically coupled to the heart through one or more of such endocardial leads. The proximal end of such leads typically is formed with a connector that connects to a terminal of the IPG or monitor. The lead body typically comprises one or more insulated conductive wires surrounded by an insulating outer sleeve. Each conductive wire couples a proximal lead connector element with a distal stimulation and/or sensing electrode. An endocardial cardiac lead having a single stimulation and/or sensing electrode at the lead distal end and a single conductive wire is referred to as a unipolar lead. An endocardial cardiac lead having two or more stimulation and/or sensing electrodes at the lead distal end and two or more conductive wires is referred to as a bipolar lead or a multi-polar lead, respectively.

In order to implant an endocardial lead within a heart chamber, a transvenous approach is utilized wherein the lead is inserted into, and passed through, the subclavian, jugular, or cephalic vein and through the superior vena cava into the right atrium or ventricle. An active or passive fixation mechanism is incorporated into the distal end of the endocardial lead and deployed to maintain the distal end electrode in contact with the endocardium position.

More recently, endocardial pacing and cardioversion/defibrillation leads have been developed that are adapted to be advanced into the coronary sinus and coronary veins branching therefrom in order to locate the distal electrode(s) adjacent to the left ventricle or the left atrium. The distal end of such coronary sinus leads is advanced through the superior vena cava, the right atrium, the ostium of the coronary sinus, the coronary sinus, and into a coronary vein communicating with the coronary sinus, such as the posterior lateral vein, mid-cardiac vein, or the great cardiac vein. Typically, coronary sinus leads do not employ active fixation mechanisms and instead rely on the close confinement within these vessels, and general lead body properties of stiffness and shape, to maintain each electrode at a desired site.

Routing an endocardial lead along a desired path to implant the electrode or electrodes in a desired implantation site, either in a chamber of the heart or in the selected cardiac vein or coronary artery, can be difficult. This is particularly true for navigating leads through the coronary sinus and into a branching vein on the left myocardium. Anomalies in the vascular anatomy and the number of branch veins associated with the anatomy make locating the desired path challenging.

Several common approaches have been developed to place electrodes within the left side of the heart. According to one approach, a guide catheter is steered into the desired location in the vasculature. A lead is then fed through the inner lumen of the catheter such that the lead electrode(s) are positioned at predetermined locations. The guide catheter may then be withdrawn. This type of approach is described in commonly assigned U.S. Pat. Nos. 6,006,137, 5,246,014, and 5,851,226 incorporated herein by reference. The described systems employ highly flexible, catheters surrounding the lead body. One difficulty with systems that completely surround the cardiac lead is that permanently implantable endocardial leads are formed typically with a proximal connector end assembly having a diameter exceeding that of the lead body. These connectors are designed to conform with an industry standard so that the connector mates with an IPG standard connector bore. Consequently, the introducer has to be made large enough to fit over the enlarged diameter connector end assembly. This detracts from the ability to advance the introducer and lead assembly through small diameter blood vessels. A smaller introducer that is designed to be split or slit may be used in the alternative, but these types of introducer are more difficult to manufacture. Yet another approach involves use of a lead without a connector end assembly, or with a smaller, non-conforming connector end assembly. Such a lead must be coupled to an adapter before it conforms to a standard, which is both inconvenient, and can result in a diminished reliability.

Another approach to lead placement involves the use of a guidewire that is steered into a desired location within the vasculature. The lead body is then tracked over-the-wire and the wire is withdrawn. According to this design, the guidewire passes through an inner lumen of the lead for an entire length of the lead. This results in a significant amount of friction that can make lead placement difficult. Additionally, since the lead must include an inner lumen for the guidewire, the size of the lead is at least somewhat dictated by the size of the guidewire. Moreover, to accomplish lead placement in this manner, the lead must be stiff enough to allow it to be advanced over the guidewire through the tortuous curves of the vasculature.

One way to minimize drag is to provide a "siderail" lead that includes means for tracking a guidewire at only a predetermined portion of the lead distal tip. This type of lead system is disclosed in U.S. Pat. No. 5,003,990, also incorporated by reference herein. This system relies on a guidewire and a carriage that releasably engages the distal electrode and is pushed along the guidewire as the lead body is pushed along the transvenous path. The guidewire is first introduced along one of the above-described desired paths, and the carriage engaging the distal electrode is placed over the proximal end of the guidewire and introduced into the blood vessel. Force is exerted against the lead body to push the carriage and the distal end of the lead body distally along the guidewire until the distal electrode is near to the desired site. The electrode is disengaged from the carriage, and the carriage is retracted along the guidewire by pulling on another wire attached to the carriage or by the retraction of the guidewire. Such retraction of the relatively bulky carriage presents the possibility of damage to an artery or vein by the carriage. Because of unintended movement of the guidewire that typically occurs during the process of disengaging the electrode from the carriage, the distal end of the lead will not necessarily be positioned at the desired implant location. As a result, some other mechanism may be needed to re-position the electrode. This adds time and complexity to the implant procedure.

In a further approach disclosed in U.S. Pat. No. 5,304,218, incorporated by reference herein, a cardiac lead is formed with a channel in the distal tip that receives a guidewire that has already been advanced through the path to the cardiac implantation site. The lead is pushed over the guidewire to the cardiac implantation site where the guidewire is withdrawn and the lead is either fixed in place or left at the cardiac implantation site. There is no disclosure of how this approach could be used to advance a cardiac lead having an active or passive fixation mechanism at or near the channel in the distal end of the lead body.

In both of the above-described approaches, the lead body must possess sufficient column strength to allow it (as well as the carriage of the '990 patent) to be pushed from the proximal end outside the patient's body and along the guidewire. The lead body diameter and/or construction materials that are required in order to make the lead body stiff enough to accomplish this over-the-wire advancement method necessarily make the lead body larger and less flexible than is desirable to withstand the rigors of chronic flexing as described above. The over-the-wire approach is classically employed in advancement of balloon catheters for Percutaneous Transluminal Coronary Angioplasty (PTCA) use which is intended to be of short duration.

Other similar over-the-wire approaches have also been disclosed. U.S. Pat. No. 6,129,749 to Bartig et al., which is incorporated herein by reference, describes a lead body having an electrode support structure at the distal tip that includes a lumen for a guidewire. The support structure is passed over the guidewire until the electrode is positioned in the desired location, and the guidewire is then removed leaving the electrode in place. U.S. Pat. No. 5,755,765 to Hyde et al., incorporated herein by reference, discloses a lead having a guide loop near the distal tip for advancing over a guidewire to an implant site. U.S. Pat. No. 5,902,331 to Bonner et al., which is incorporated herein by reference, describes a tracking mechanism that may be coupled to a lead body, and that may be pushed via a pusher over an elongated guide body to a desired implant site. U.S. Pat. No. 5,803,928 to Tockman et al., which is incorporated herein by reference, discusses an over-the-wire pacing lead having a side access port for being slid over a guidewire to a desired implant position.

One problem with the systems described in the foregoing patents is that no anchoring mechanism is provided to maintain the guiding device such as the guidewire in a stationary position while the leads are being advanced to the desired implant site. This can cause the guidewire to become dislodged. What is needed is some type of anchoring mechanism that can be utilized while one or more leads are steered into position. This anchoring mechanism must be retractable so that the guiding device may be withdrawn from the vasculature without disrupting lead placement. Ideally, the guiding device could also be used to facilitate fixation of the electrode to the vasculature.

SUMMARY OF THE INVENTION

The current invention provides an improved system and method for deploying medical electrical leads. According to one embodiment, a guiding device such as a guidewire is used to navigate the vascular system of a body. The guiding device includes a fixation member that can be deployed to maintain the guiding device at a desired location within the vascular system. The fixation member may be an inflatable device such as a balloon. Alternatively, the fixation member may be an expandable device constructed of flexible fibers that has both an expanded and a contracted state.

According to another aspect of the invention, the system includes a coupling member located adjacent to the guiding device. For example, the coupling member may be a rail extending between the proximal end of the guiding device and a point proximal to the fixation member. The coupling member is adapted to slidably engage an electrode assembly in a manner that allows the electrode assembly to be deployed from the distal end of the coupling member. The electrode assembly may be advanced to the distal end of the coupling member by applying force to a lead coupled to the electrode assembly, or by utilizing a pusher rod. According to one aspect of the invention, the rail member may include means to prevent the electrode from twisting laterally around the rail member as the electrode assembly is deployed. During electrode deployment, the guide device is maintained at a stationary location via the fixation member.

To deploy additional electrodes, the fixation member may be placed in a partially contracted or deflated state and the guiding device re-positioned. When located at a second predetermined implant site, the fixation mechanism is again deployed to stabilize the position of the guiding device. Then another electrode may be deployed in the manner discussed above.

In one embodiment of the invention, the coupling member slidably engages the guiding device. For example, the coupling member may be a rail member that slidably engages a channel of the guiding device. In this embodiment, the rail member may be readily re-positioned to multiple implant sites to deploy more than one electrode while the fixation mechanism remains stationary within a patient's vascular system. In an alternative embodiment of the invention, the coupling member is a channel included in the body of the guiding device adapted to engage a coupling member located on an electrode assembly.

According to one aspect of the invention, the guiding device includes a lumen to deliver a contrast agent such as ISOVUE® (iopamidol) flouro visible medium to the environment surrounding the guiding device. This allows a patient's vascular system to be viewed using a fluoroscope so that more accurate lead placement may be accomplished. In one embodiment of the system, the lumen is included within the coupling mechanism.

Other scopes and aspects of the invention will become apparent to those skilled in the art from the following description and the accompanying drawings.

BRIEF DESCRIPTION OF THE DRAWINGS

FIG. 1C is a cross-section view of the guidewire of FIG. 1B at line 1C—1C.

FIG. 1D is a cross-section view of the guidewire of FIG. 1B at line 1D—1D.

FIG. 1E is a cross-section view of the guidewire of FIG. 1B at line 1E—1E.

FIG. 4 is a cross-sectional view at line 4—4 of FIG. 1 illustrating the side rail design coupled to an electrode assembly.

FIG. 12A is a cross-sectional view illustrating another embodiment of the guidewire that includes a second lumen for delivering fluoro visible media.

FIG. 12B is a cross-sectional view illustrating another embodiment of the guidewire of FIG. 12A wherein the lumen for delivering fluoro visible media is included in a side rail.

DETAILED DESCRIPTION OF THE PREFERRED EMBODIMENT

The current invention provides a system and method for introducing one or more electrodes into cardiac veins or coronary arteries. The system includes a low profile guiding device having a fixation mechanism at the distal tip for anchoring the guiding device in position while one or more electrodes are advanced over the body of the guiding device. In one embodiment, the fixation mechanism is capable of retracting such that it is co-axial with the guiding device for easy withdrawal of the device after electrode placement is complete.

Figure 1A:
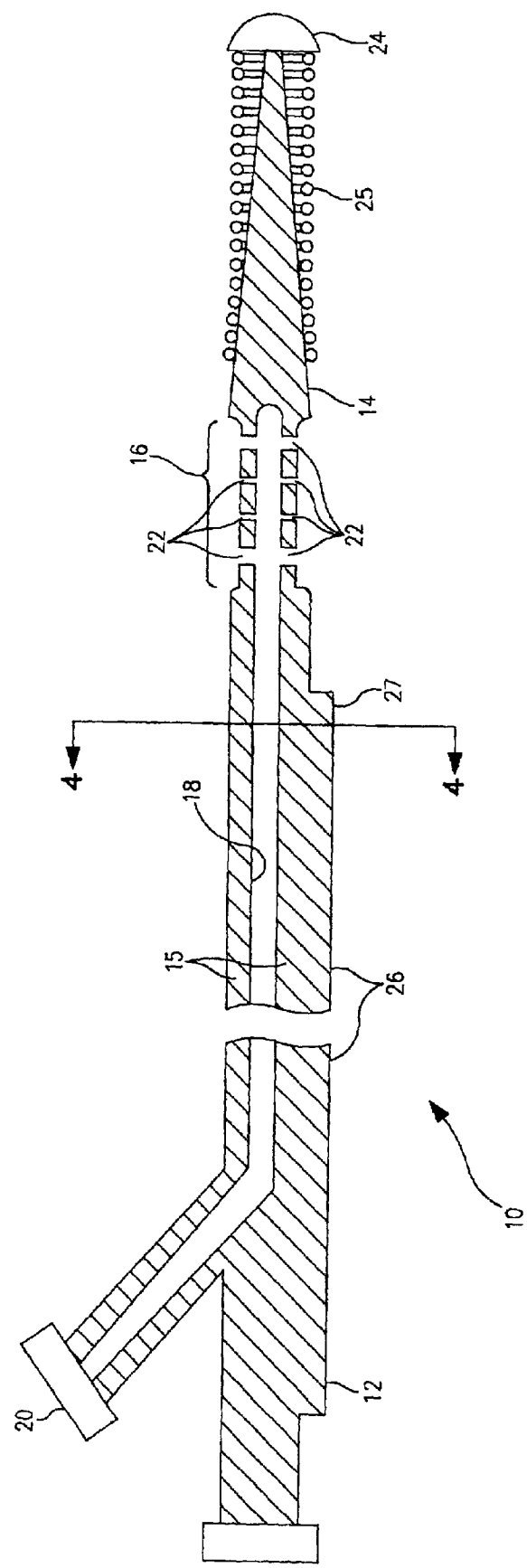
FIG. 1A is a cross-sectional side view of a guidewire including a siderail.

FIG. 1A is a cross-sectional side view of a guidewire 10 including a proximal end portion 12 and a distal end portion 14, which may be of a standard length of 175–310 cm long, or which may be of a non-standard length. The guidewire of the preferred embodiment has an elongated tubular body 15, and may have an outer diameter of between 0.014 and 0.038 inches at the proximal end portion. Preferably, the outer diameter of the proximal end portion is approximately 0.018 inches. The tubular body 15 may be formed of a flexible metal tubing, which may be a superelastic alloy such as nitinol tubing commercially available from Shape Memory Applications, Inc. of Santa Clara, Calif. or Raychem Corporation of Menlo Park, Calif.

The nitinol tubing includes a narrowed region 16 that may be created using a machining or etching process to form a portion of the tubing with a decreased diameter that is between approximately 0.003–0.010 inches smaller than the rest of the tubing. The narrowed region in one embodiment may be between approximately 0.010 and 1 inch long. The nitinol tubing may further include an inflation lumen 18 extending from an inflation port 20 located at the proximal end portion 12 to the narrowed region 16. The inflation lumen is coupled to the external surface of the narrowed region 16 by one or more openings 22, as will be described further below.

In one embodiment, distal end portion 14 of guidewire 10 is a tapered atraumatic distal tip that is terminated with a rounded tip fixture 24. The distal end of the tapered tip may have a diameter ranging from approximately 0.010 to 0.030 inches. This reduced tip stiffness helps prevent perforation of the coronary vasculature during guidewire placement. Variable stiffnesses at the distal tip can be achieved by step grinding tapers of differing diameters. The flexible tip may be reinforced with a spring coil 25 having a diameter that provides a constant outer diameter for the distal end portion 14 of guidewire 10. This coil, which is preferably formed of a platinum wire, may be welded, soldered, or bonded with a medical grade epoxy to the rounded tip fixture 24 and to the distal end portion 14. Alternatively, a stainless steel or nitinol wire may be used. Non-tapered versions of the guidewire distal tip may also be employed, such as those shown and described in commonly-assigned U.S. Pat. Nos. 5,746,701 and 5,916,178 to Noone et al., both incorporated herein by reference in their entirety. In one embodiment, the guidewire may include a lubricious coating such as PTFE to reduce the coefficient of friction when the guidewire is placed in the vascular system.

Guidewire 10 may further include a coupling member such as side rail 26 that extends from the proximal end of the guidewire to distal end 27 of side rail located proximal to the narrowed region 16. This side rail 26 is designed to engage an electrode structure in a manner to be discussed further below. The side rail may also include a lubricious coating in the manner discussed above.

Figure 1B:
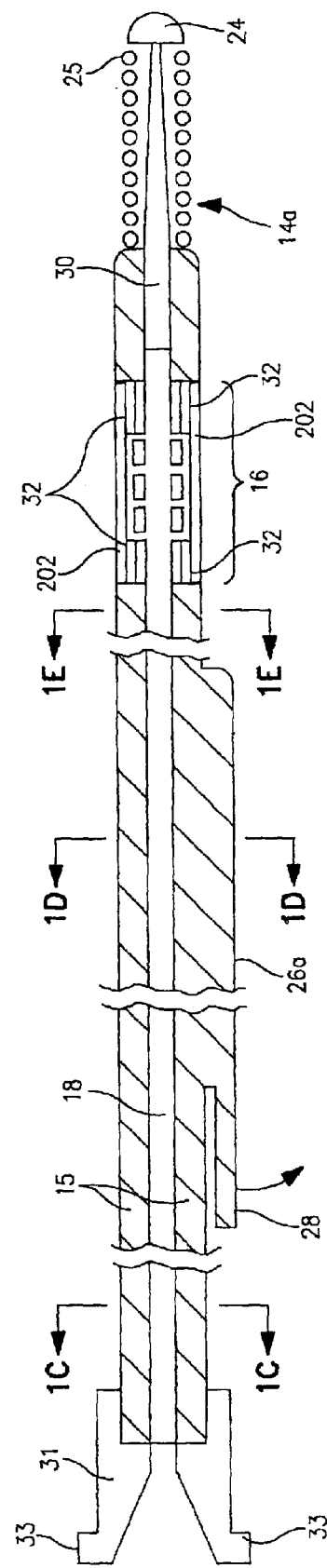
FIG. 1B is a cutaway side view of another embodiment of the guidewire including a siderail.

FIG. 1B is a cutaway side view of another embodiment of the guidewire. This embodiment includes a side rail 26A that has a flexible extension 28 at the proximal end that is not coupled to the body of the guidewire. This extension may be flexed away from the guidewire body to allow an electrode assembly to be more readily loaded onto the siderail in a manner to be discussed below. The embodiment of FIG. 1B further includes a distal end portion 14A that includes a wire 30 surrounded by spring coil 25, and including a rounded tip fixture 24. The wire, which may be formed of a shape memory alloy such as nitinol, is attached by fitting the proximal end of the wire into lumen 18 of the guidewire. The wire may be attached via welding, soldering, brazing, or using a medical adhesive. This embodiment of the distal end portion 14A has the advantage of not requiring a machining process such as step-grinding. The proximal end of guidewire is coupled to a hub 31 having a luer taper and grip members 33. Finally, this Figure illustrates a layer of epoxy 32 or a medical adhesive, deposited in the narrowed region 16 to adhere to a flexible sheath 202 in a manner to be discussed further below.

FIG. 1C is a cross-section view of the guidewire of FIG. 1B at line 1C—1C. This view illustrates inner lumen 18 and elongated tubular body 15. This view further illustrates hub 31 with the grip members 33.

FIG. 1D is a cross-section view of the guidewire of FIG. 1B at line 1D—1D. This view illustrates inner lumen 18, elongated tubular body 15, and side rail 26.

FIG. 1E is a cross-section view of the guidewire of FIG. 1B at line 1E—1E. This view includes inner lumen 18, and further shows the distal end 27 of the side rail 26.

Figure 2:
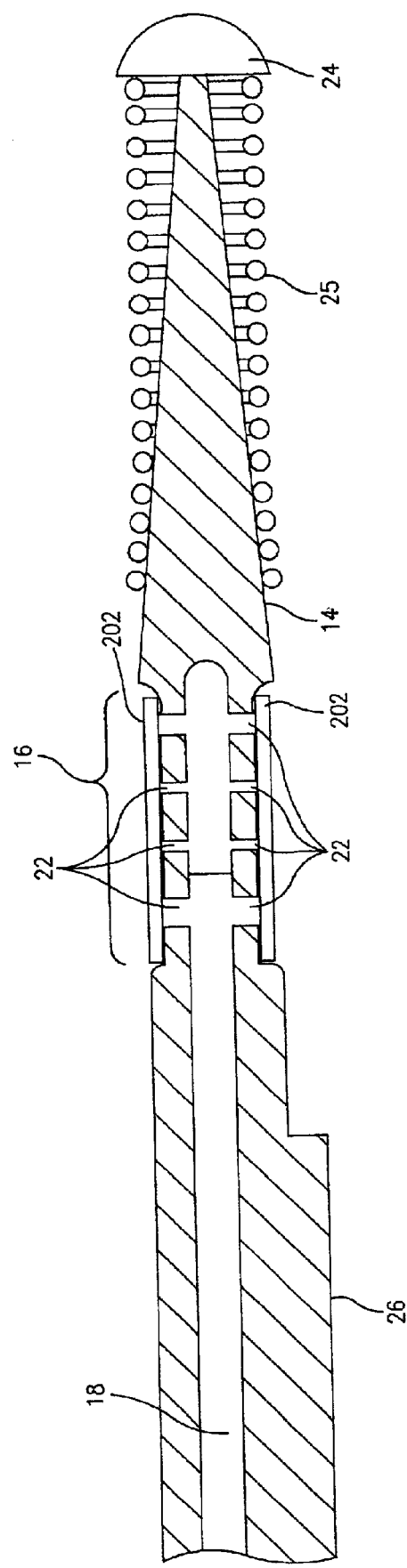
FIG. 2 is a cutaway, enlarged side view of a guidewire, including a flexible sheath bonded to the distal end portion of the guidewire.

FIG. 2 is a cutaway side view of guidewire 10, and further shows a sheath 202 bonded to narrowed region 16. In the preferred embodiment, sheath 202 is selected to have a thickness that matches the depth of the narrowed region so that the outer surface of the sheath is substantially co-planar with the outer surface of the guidewire. The sheath may be comprised of a material having a very high elastic limit. Examples of such materials include synthetic polyisoprene latex HT-300 having a thickness of approximately 0.002 to 0.004 inches. Other suitable materials include SIS/SBS copolymer blend, also having a thickness of approximately 0.002 to 0.004 inches. Both of these materials are commercially available from Apex Medical Technologies, Incorporated. The sheath is bonded to the guidewire at both the proximal and distal ends of the narrowed region 16 using a bonding agent such as cyanoacrylate. For example, Superbonder 4981 cyanoacrylate commercially available from the Loctite Corporation may be used for this purpose.

Referring to FIGS. 1A and 2, the sheath may be inflated with a fluid, which is preferably a gas, by inserting a syringe in inflation port 20. Because the sheath is formed of a highly elastic material, the inflated sheath, which forms an inflated, or balloon-like, structure, expands sufficiently to contact the wall of a vessel in which it is positioned. This provides a fixation means that maintains the guidewire in a fixed position as will be discussed below. The highly elastic properties of sheath 202 also allow the balloon to deflate such that the outer surface of the sheath is substantially co-axially aligned with the outer surface of the guidewire to thereby provide a very small profile.

Figure 3:
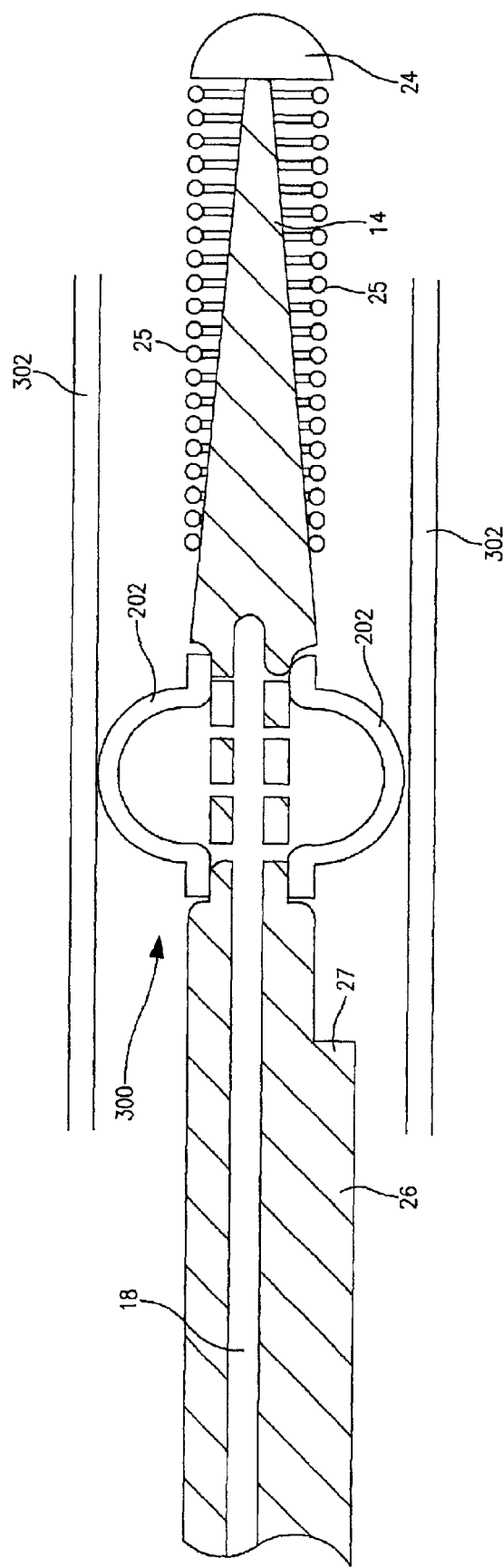
FIG. 3 is a cutaway side view of guidewire located within a vessel of a body and with sheath inflated to form a balloon that contacts the walls of the vessel.

FIG. 3 is a cutaway side view of guidewire 10 with sheath 202 inflated to form balloon 300, which contacts the walls of vessel 302. This contact maintains the guidewire at the implant site during deployment of electrodes.

As discussed above, the guidewire assembly of the current invention is designed to slidably engage an electrode, which may then be advanced to a predetermined implant site. In one embodiment of the invention, the side rail 26 is provided to engage the electrode assembly.

FIG. 4 is a cross-sectional view at line 4—4 of FIG. 1A illustrating the side rail design coupled to one embodiment of an electrode assembly. FIG. 4 illustrates tubular body 15 of the guidewire 10 surrounding inflation lumen 18. Tubular body is coupled to, or alternatively formed to include, a side rail structure 26. This side rail 26 is adapted to couple to electrode assembly 400 in the manner shown.

Electrode assembly 400 includes an inner channel 401 and an opening 402 adapted to slidably engage the side rail 26. This allows the electrode assembly to slide over the side rail 26 to a desired implant site. For example, a push rod assembly (not shown in FIG. 4) may be used to engage the electrode assembly 400 and push the assembly to an implant site in a manner to be discussed further below.

Electrode assembly may incorporate any type of electrode configuration known in the art. For example, it could be a steroid-eluting porous pacing electrode, as described in U.S. Pat. No. 4,506,680 to Stokes, and related U.S. Pat. Nos. 4,577,642; 4,606,118; and 4,711,251. In one embodiment, the electrode is formed of a material such as a shape memory alloy that may be temporarily deformed without losing an initial, trained state. As shown in FIG. 4, the electrode outer diameter may be considerably larger than the outer diameter of the guidewire.

The electrode assembly may include flexible fixation members shown as tines 404 in FIG. 4. As illustrated in FIG. 4, these tines are folded around the body of electrode assembly in a closed, non-deployed position when electrode assembly is loaded onto side rail 26. A bottom surface 408 of tubular member 15 retains the tines 404 in this position until the electrode is deployed in a manner to be discussed below. When the electrode assembly is deployed, the tines unfold to a deployed position 410 (shown dashed) as illustrated by arrows 405. In this deployed position, the tines contact tissue such as the vessel walls of a cardiac vein, allowing the electrode assembly to maintain a stationary position at the site of implant. Preferably, these tines are formed of a material such as superelastic alloy that may be deformed temporarily while ultimately retaining an initial trained shape.

In one embodiment, electrode assembly is formed of a material that has elastic properties to allow it to be deformed while retaining an initial memorized shape. For example, the electrode assembly may be formed of a superelastic alloy such as Nitinol. In this embodiment, the electrode assembly assumes a closed tubular configuration when the electrode is not loaded on guidewire 10. This closed configuration may be expanded along a longitudinal seam to form opening 402, thereby allowing the electrode assembly to be slid along side rail 26 during deployment. However, after deployment, the electrode assembly again re-assumes the closed tubular shape. This is desirable because the closed tubular configuration prevents excess tissue in-growth around the electrode assembly that would make lead extraction difficult.

Figure 5B:
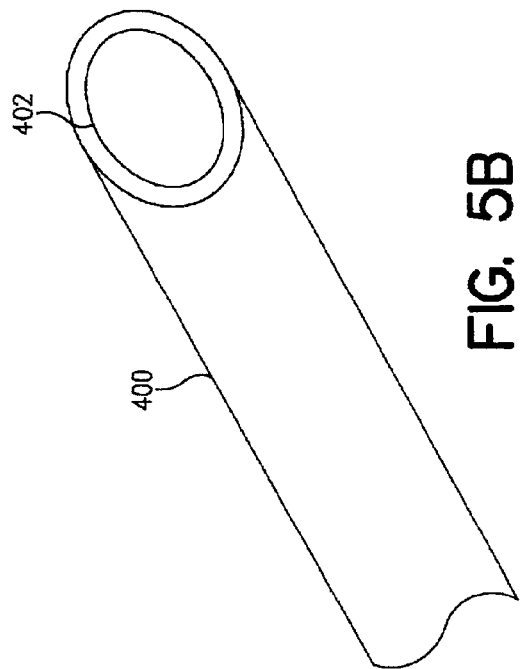
FIG. 5B is a perspective side view of electrode assembly when opening is closed.
Figure 5C:
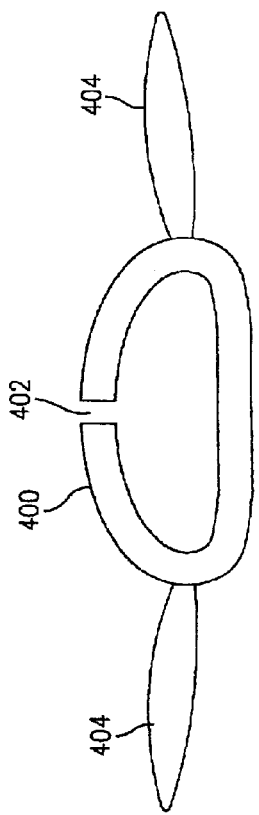
FIG. 5C is a cross-sectional end view of the electrode assembly illustrating the manner in which tines extend when the electrode assembly is deployed.
Figure 5A:
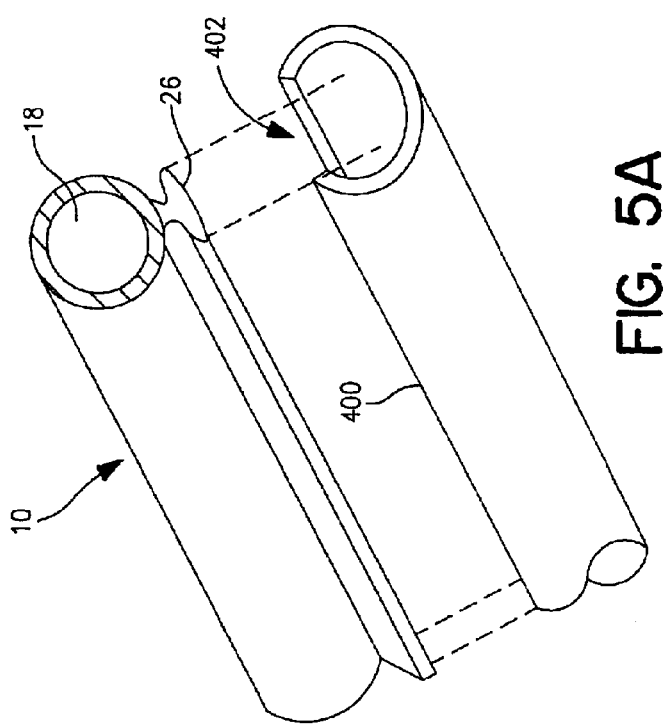
FIG. 5A is a perspective side view of electrode assembly when the opening of the electrode assembly is in an expanded state to load the electrode assembly onto a guidewire.

FIG. 5A is a perspective side view of the guidewire 10 and the electrode assembly. Opening 402 is in an expanded state as is needed when the assembly is loaded onto the guidewire.

FIG. 5B is a perspective side view of electrode assembly when opening 402 is closed as occurs after deployment in one embodiment of the invention.

FIG. 5C is a cross-sectional end view of electrode assembly 400 illustrating the manner in which tines 404 extend when the electrode assembly is deployed. These tines contact the walls of the vessel at the site of implant to stabilize the electrode assembly until tissue in-growth begins.

Figure 6:
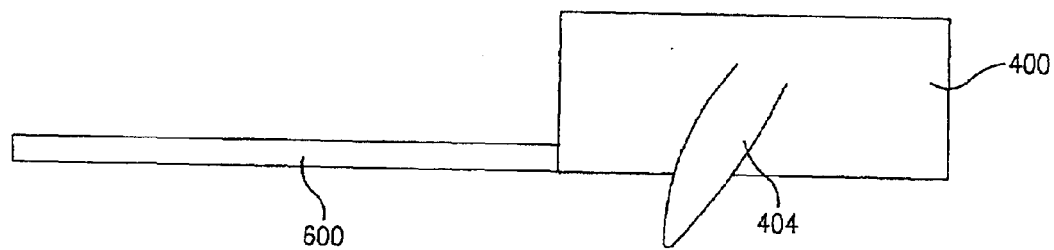
FIG. 6 is a side plan view of the electrode assembly, and further illustrates lead body coupled to the electrode assembly.

FIG. 6 is a side plan view of electrode assembly 400, and further illustrates lead body 600 coupled to the electrode assembly. Lead body may be of any construction known in the art, and carries a conductor (not shown in FIG. 6) that is coupled to electrode assembly 400. This conductor is also coupled to a connector pin residing at the proximal end of lead body. The conductor may be a coil, a single or multi-filar cable, or any other type of conductor suitable for this purpose.

As discussed above, the current inventive guidewire may be used to reliably place one or more leads at a predetermined implant site. First, the guidewire must be navigated to the desired implant site. This may be accomplished with, or without, the aid of a guide catheter. If the former approach is to be utilized, any guide catheters of conventional design may be selected, including the catheters described in commonly assigned U.S. Pat. Nos. 6,006,137 and 5,246,014 referenced above. Some guide catheter suitable for use in placing guidewire 10 may include a steering mechanism such as pre-formed or shapeable distal tip, or alternatively, one or more pull wires in the side walls. Using this steering mechanism, the guide catheter is navigated to a desired implant site such as within the coronary sinus or a branch vein. The guidewire 10 may then be advanced within the inner lumen of the catheter to the site of implant, and the guide catheter may be withdrawn from the patient's body.

Once at the general site of implant, the position of the guidewire 10 is adjusted so that distal end 27 of side rail 26 is at the predetermined implant site for a first electrode assembly. As discussed above, distal end 27 of side rail 26 may include a coating of, or alternatively may be formed of, a material that is visible under a fluoroscope to aid in this positioning step. The guidewire is maintained at the site of implant by injecting a fluid, which is preferably a gas, into inflation lumen 18 via inflation port 20 to inflate balloon 300. Then, in one embodiment of the invention, electrode assembly 400 is loaded onto a proximal end of side rail 26. A pusher rod is employed to push the electrode assembly over the length of the side rail 26 and off the side rail distal end 27 so that the electrode is deployed.

As discussed above, in one embodiment, the electrode assembly may include flexible self-expanding tines 404 that are held in a folded, semi-closed, position by bottom side 408 of elongated tubular body 15 when the electrode is loaded onto the side rail 26. This is illustrated in FIG. 4. After the electrode is pushed from the distal end 27 of side rail 26, the tines unfold in the manner shown in FIGS. 4 and 5C to contact the walls of a vessel. The tines may be formed of a superelastic alloy such as Nitinol, for example, such that the tines assume a trained position when not restrained by the bottom side 15 of the elongated tubular body 15.

In one embodiment of the invention, balloon 300 may be used to further secure tines 404 within a vessel wall. This is accomplished by partially deflating balloon 300, then moving the balloon proximate to electrode assembly 400 within the vessel. Balloon 300 is then re-inflated, which applies force against the electrode assembly 400, embedding the tines further into the vessel wall. The balloon may then be partially, or entirely, deflated so that the guidewire may be re-located.

To further deploy additional electrodes, the balloon 300 is partially, or entirely, deflated and the guidewire 10 is moved so that distal end 27 of side rail 26 is located at a second implant site. Most preferably, the second implant site is located at a proximal position within the vessel as compared to the first implant site. A second electrode assembly may be loaded onto side rail 26 in the manner discussed above, and the pusher may be used to deploy the electrode assembly as previously described. Multiple electrode assemblies may be deployed in this manner.

The above-described guidewire requires at least partial deflation of the balloon and movement of the guidewire 10 to deploy multiple electrodes. In another embodiment of guidewire 10, side rail 26 is slidably coupled to tubular body 15. This allows distal end of side rail 26 to be moved without deflating and re-locating balloon 300.

Figure 7A:
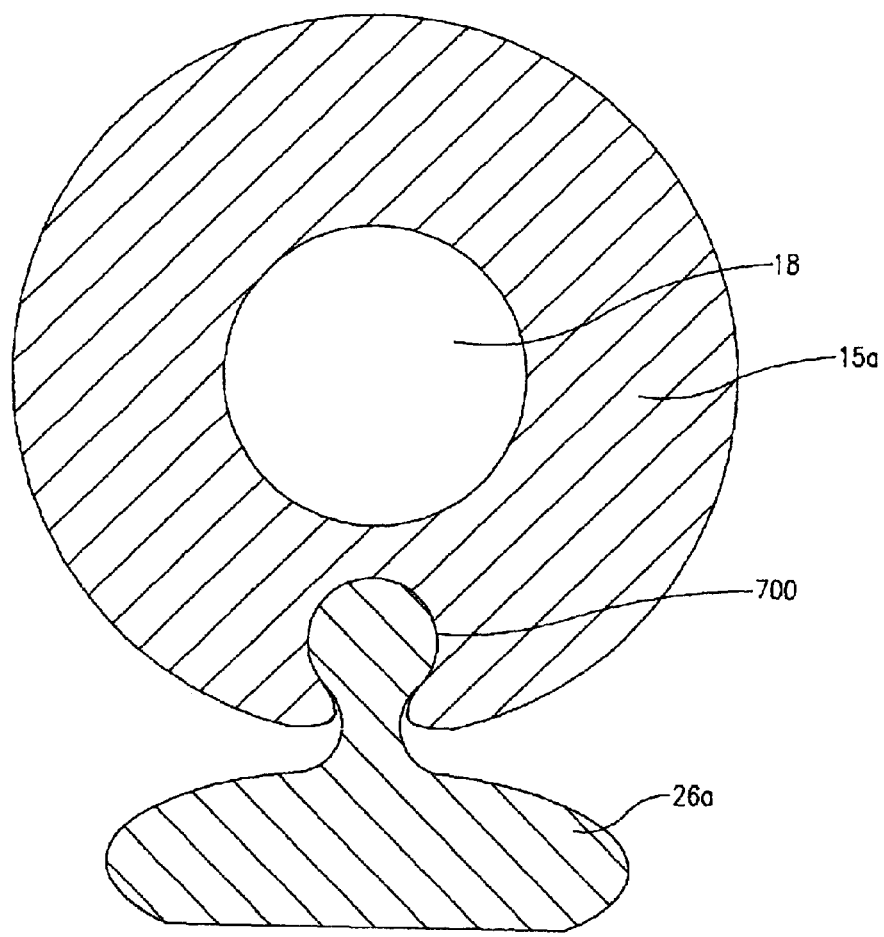
FIG. 7A is a cross-sectional view of a guidewire wherein the side rail is slidably coupled to the guidewire.

FIG. 7A is a cross-sectional view of another embodiment of guidewire 10 illustrating a side rail that is slidably coupled to guidewire 10. Side rail 26a slidably engages a channel 700 in tubular body 15a. After a first electrode assembly is deployed, the proximal end of side rail 26a, which remains outside of the body during the implant procedure, may be slid in a proximal direction. When the distal end 27 of side rail 26a is at the second site of implant, another electrode may be deployed in the manner discussed above. No movement of the guidewire, or deflation of the balloon is necessary to accomplish re-selection of another implant site. In this embodiment, the proximal end of the side rail may be fitted with a fastening member such as snap-fit connectors or other suitable connection means to allow the side rail to be temporarily fastened to the guidewire, thereby maintaining the distal end of the side rail at a predetermined implant site during electrode deployment. This is discussed further below with respect to FIG. 7F.

Figure 7D:
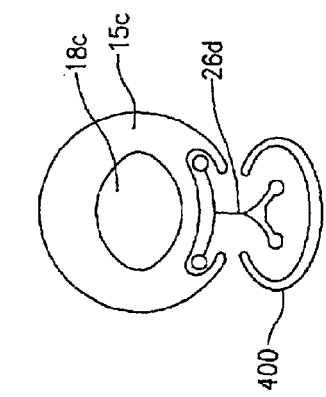
FIG. 7D is a cross-sectional view of a guidewire having a slidable side rail formed in an "K" configuration.
Figure 7C:
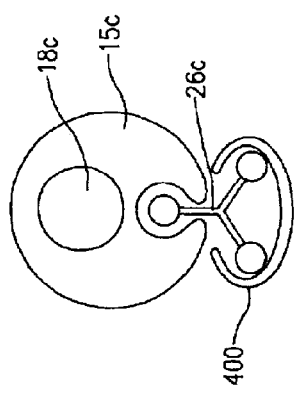
FIG. 7C is a cross-sectional view of a guidewire having a slidable side rail formed in an "Y" configuration.
Figure 7E:
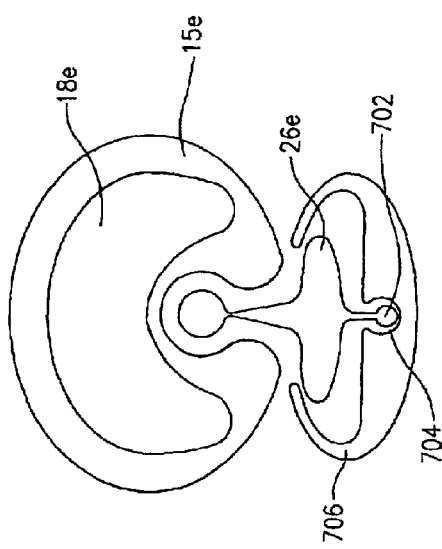
FIG. 7E is a cross-sectional view of a guidewire having a slidable side rail having a second rail to engage an electrode assembly.
Figure 7B:
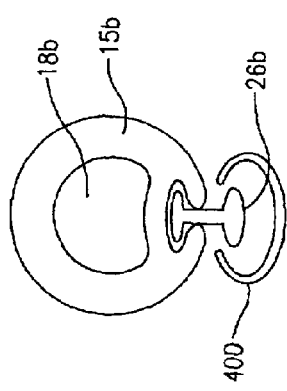
FIG. 7B is a cross-sectional view of a guidewire having a slidable side rail formed in an "H" configuration.

Many other embodiments of guidewire may be provided for coupling to an electrode assembly, some of which are shown in FIGS. 7B through 7D.

FIG. 7B is a cross-sectional view of a guidewire having a side rail 26b formed in an "H" configuration. This view further shows inner lumen 18b having a shape which is not circular. This allows for uniform wall thickness in elongated tubular body, simplifying the manufacturing process and providing a more stable structure.

FIG. 7C is a cross-sectional view of a guidewire having a side rail 26c formed in a "Y" configuration.

FIG. 7D is a cross-sectional view of a guidewire having a side rail 26d formed in a "K" configuration. This configuration also includes an inner lumen 18d which is not circular, and which has an inner diameter that is offset from the center of the guidewire.

FIG. 7E is a cross-sectional view of a guidewire having a slidable side rail 26e, wherein the side rail has a second rail 702 to engage a channel 704 in electrode assembly 706. The coupling of the channel 704 to the rail 702 prevents the electrode assembly 706 from twisting or shifting in a lateral direction as it is guided along slidable side rail 26e.

Figure 7F:
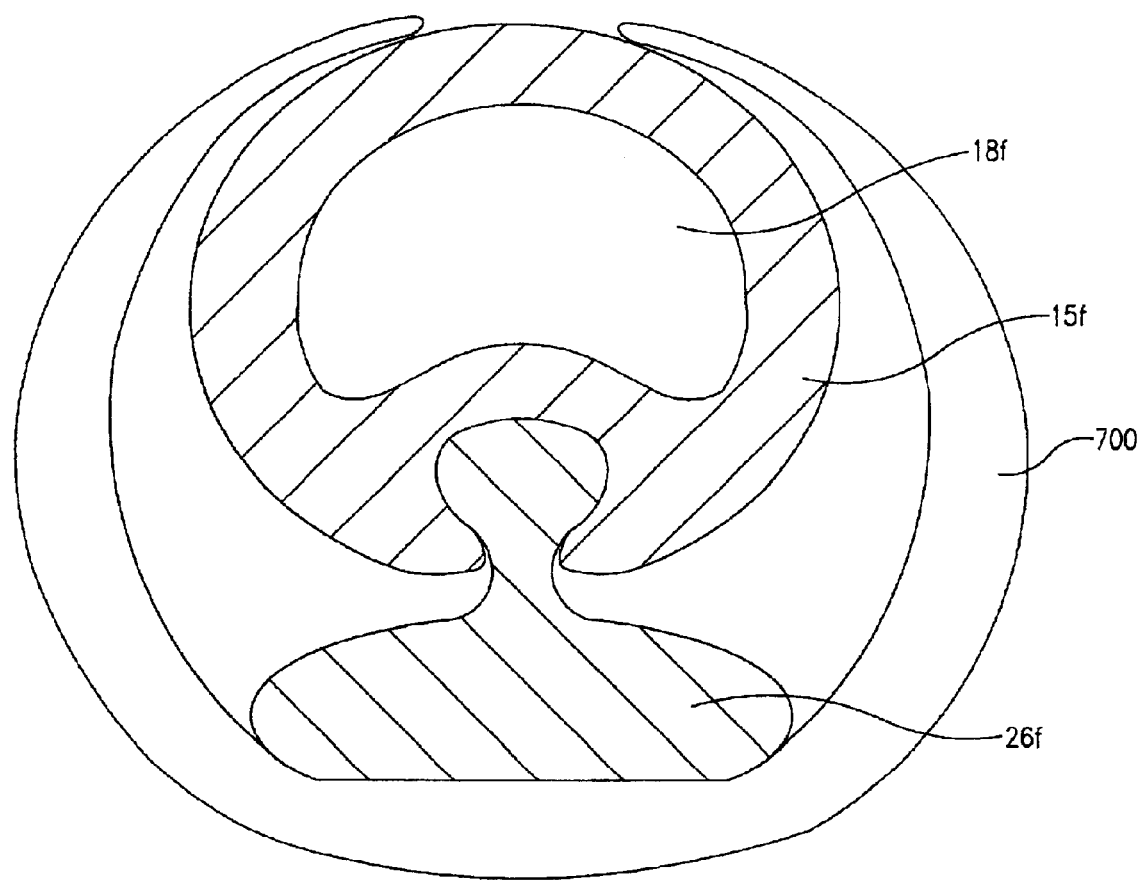
FIG. 7F is a cross-sectional view of a slidable side rail at line 7F—7F of FIG. 1 and further illustrates a fastening device to maintain the side rail at a predetermined position with respect to the guide wire.

FIG. 7F is a cross-sectional view of a slidable side rail 26f, and further illustrates a clamping mechanism to hold the side rail in a stationary position relative to the tubular body of the guidewire. After the distal end of the side rail 26f is positioned at a predetermined implant site during a lead implant procedure, clamp 700 may be positioned over a proximal portion of both the tubular body 15f and side rail 26f. This maintains the side rail is a stable position with respect to the tubular body, and prevents the side rail from being pushed in a distal direction as the electrode assembly is pushed along the side rail. Clamp 700 may be a deformable "C" clamp, or any other type of clip mechanism that may be temporarily deformed but that substantially retains an initial shape. Other fastening means may be used to temporarily maintain the position of the side rail during electrode deployment.

In all of the embodiments having a slidable side rail, the side rail may be formed of die-drawn MP-35N, die-drawn nitinol, an extruded polyetheretherketone (PEEK) polymer (VICTREX® 381G or VICTREX® 450 manufactured by Victrex PLC), or any other similar suitable materials.

Figure 8:
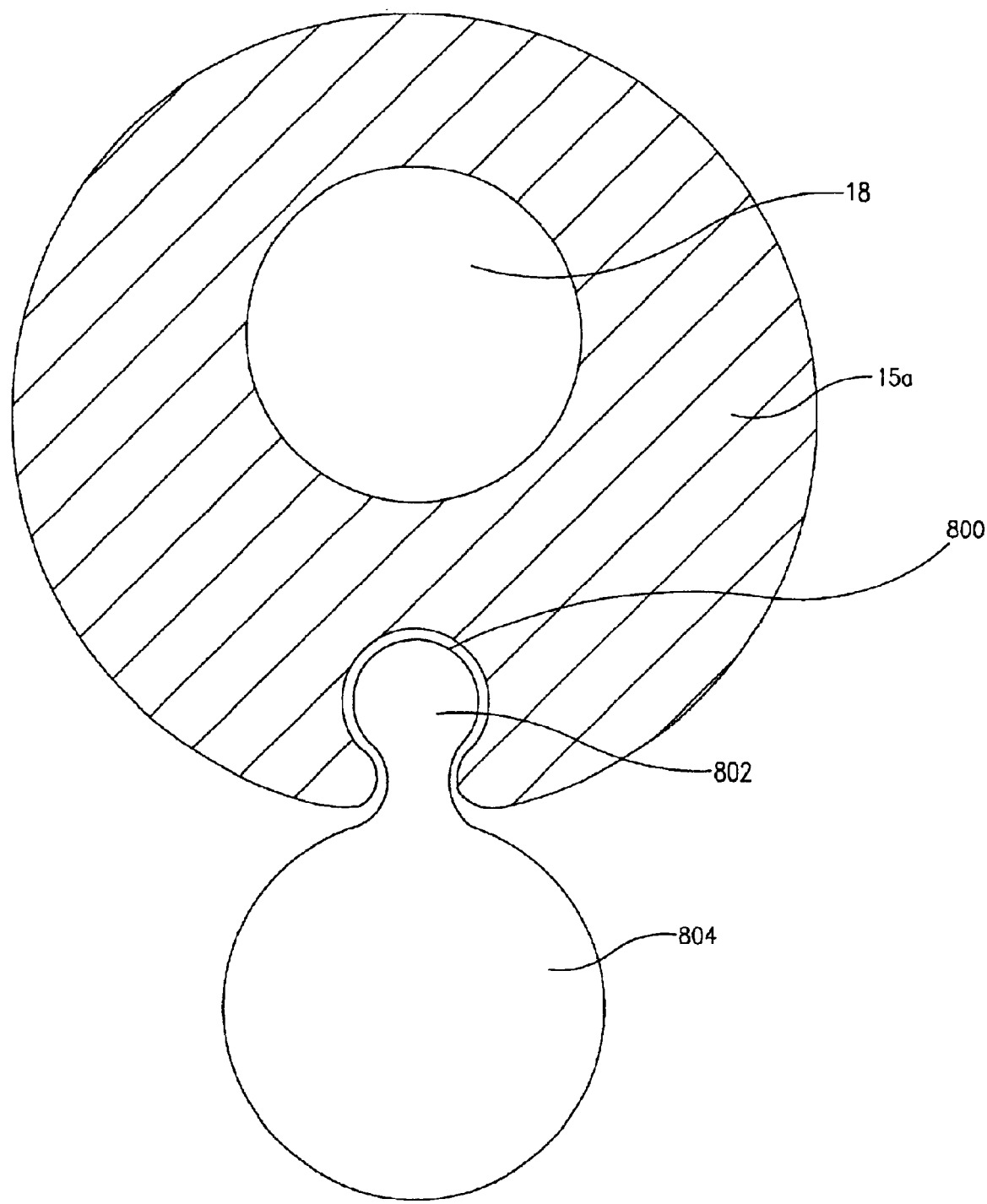
FIG. 8 is a cross-sectional view of an electrode assembly including a side rail.

FIG. 8 is a cross-sectional view of a guidewire without a side rail 26. In this embodiment, a longitudinal channel 800 extending from the proximal end of guidewire 10 to a location on guidewire 10 that is proximal the balloon 300 is provided to engage a rail or protrusion 802 that is coupled to, or integral with, the electrode assembly 804. At the distal end of channel 800, channel sides are cutaway so that electrode assembly 804 disengages the channel at this location and is deployed. In this embodiment, movement of the guidewire is required to select additional sites of implant.

In one embodiment of the invention, hollow electrode assemblies may be deployed over the guidewire itself. According to this method of deployment, one or more hollow electrode assemblies are fed over the guidewire with a pusher rod. The pusher rod is preferably manufactured from a material having a low friction coefficient and possesses high pushability. Suitable materials include PTFE loaded with PEEK, PEEK, FEP, or PTFE. The pusher rod also preferably includes an atraumatic distal tip such as a rolled distal tip wherein the material at the end is rolled back upon itself.

When hollow electrode assemblies are employed with the current invention, a first electrode assembly may be positioned at a first implant site along the guidewire 10 that is proximal to the inflated balloon 300, but which is more distal than the other implant sites. Next, a second electrode assembly may be located along the guidewire at the next most distal implant site. This may be repeated for one or more additional electrode assemblies. When the electrode assemblies have been positioned, the balloon 300 is deflated and the guidewire is pulled through the lumens of the electrode, leaving the electrodes in the desired locations. It may be noted that in this embodiment, it is important that the fixation mechanism, which in this example is the balloon 300, is isodiametric with respect to tubular body 15 so that the electrode positions are not disturbed, and the guidewire is easily pulled through the lumens of the electrodes. That is, the balloon material must not be inflated such that the sheath 202 exceeds its elastic limit and does not retract completely to its original uninflated shaped without any residual deformations. As noted above, it is therefore important that the sheath 202 is formed of a material having a very high elastic limit.

In one embodiment of the invention involving guidewire 10 that may have an outer diameter of 0.014 to 0.018 inches, the guidewire may be employed to deploy one or more instances of an over-the-wire lead such as the Model 4193 lead available from Medtronic Corporation. In this case, no pusher rod is necessary since the lead is sufficiently pushable.

Figure 9:
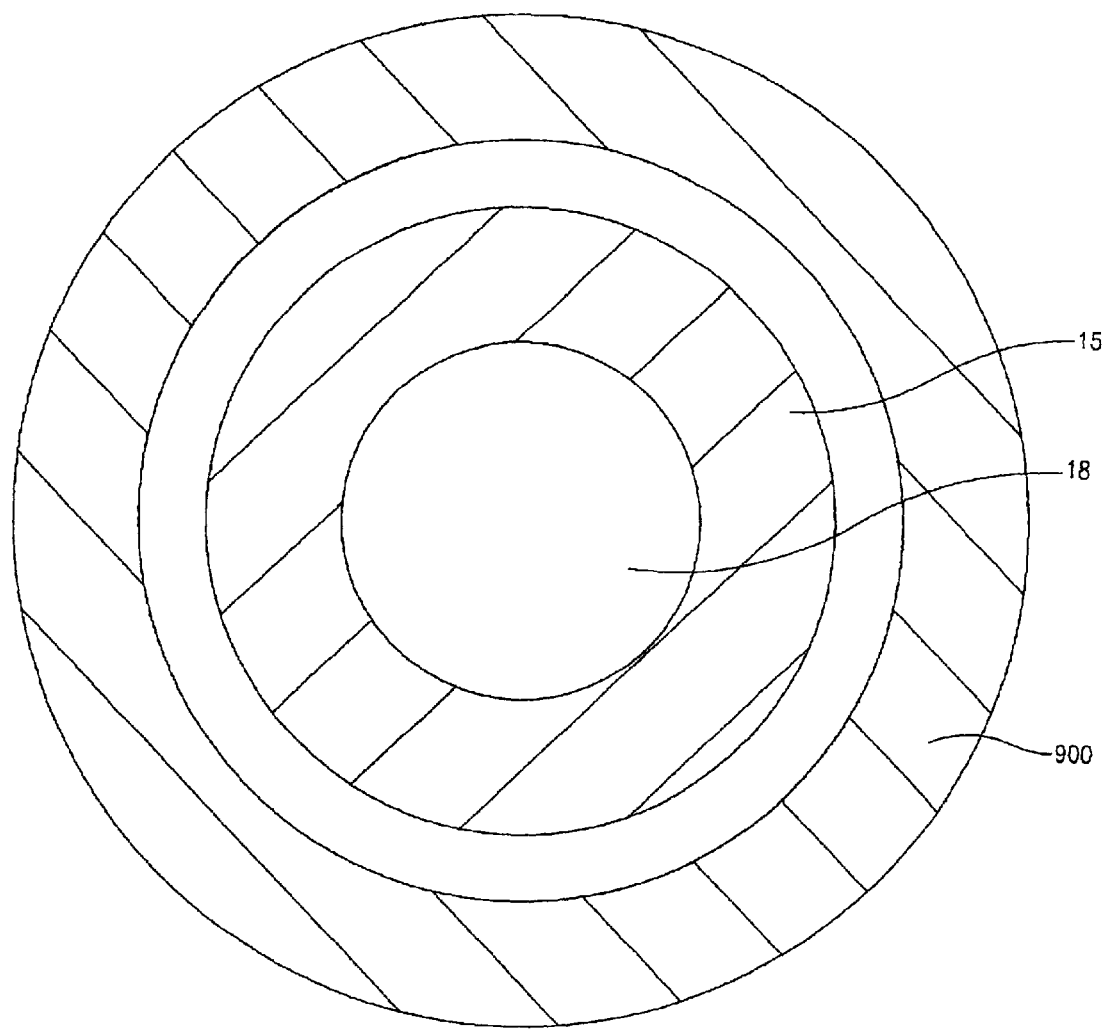
FIG. 9 is a cross-sectional view of a tubular electrode assembly positioned over the guidewire of the current invention.

FIG. 9 is a cross-sectional view of a tubular electrode assembly 900 positioned over guidewire 10.

Figure 10:
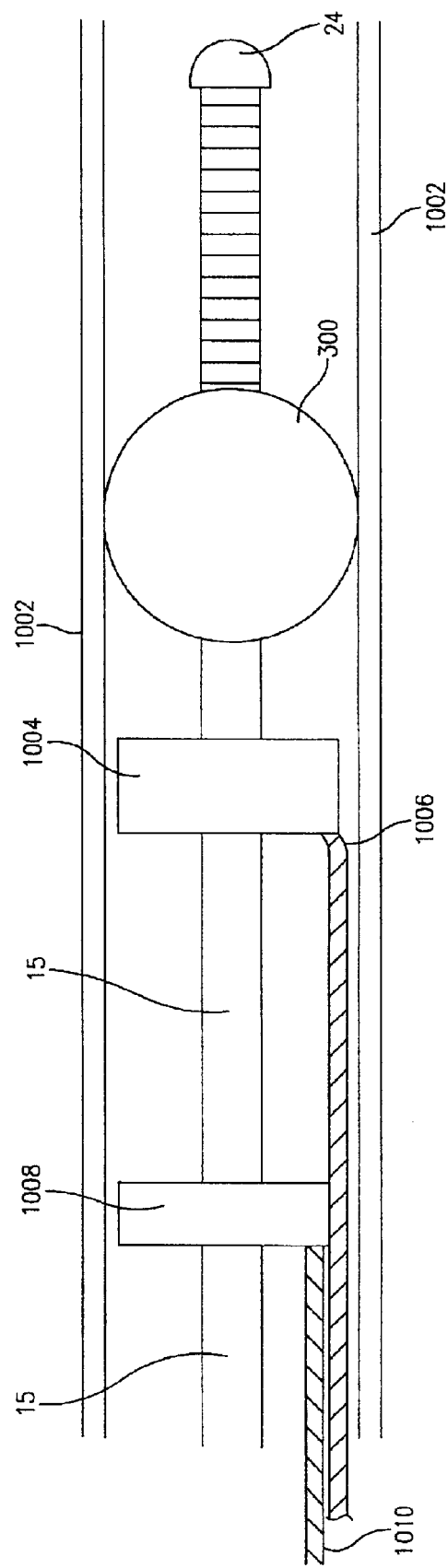
FIG. 10 is a plan view of guidewire within a vessel with multiple electrode assemblies positioned over the guidewire at various implant sites within the vessel.

FIG. 10 is a plan view of guidewire 10 within a vessel 1002 with multiple electrode assemblies positioned at various implant sites prior to deployment of the electrode assemblies. A first electrode assembly 1004, which is shown coupled to lead 1006, is positioned proximal to balloon 300. A second electrode assembly 1008, shown coupled to lead 1010, is located more proximal to electrode assembly 1004. Additional electrode assemblies may be positioned along guidewire 10. In one embodiment, the electrode assemblies may be of different sizes. For example, it may be desirable to substantially match the outer diameter of the electrode assembly with the diameter of a vessel at the location at which the electrode assembly will be placed. Alternatively, it may be desirable to select smaller electrode assemblies to be positioned at the more proximal positions on the guidewire. The smaller electrode assemblies are able to accommodate the various leads located in the veins that are coupled to the more distally-located electrodes.

Figure 11:
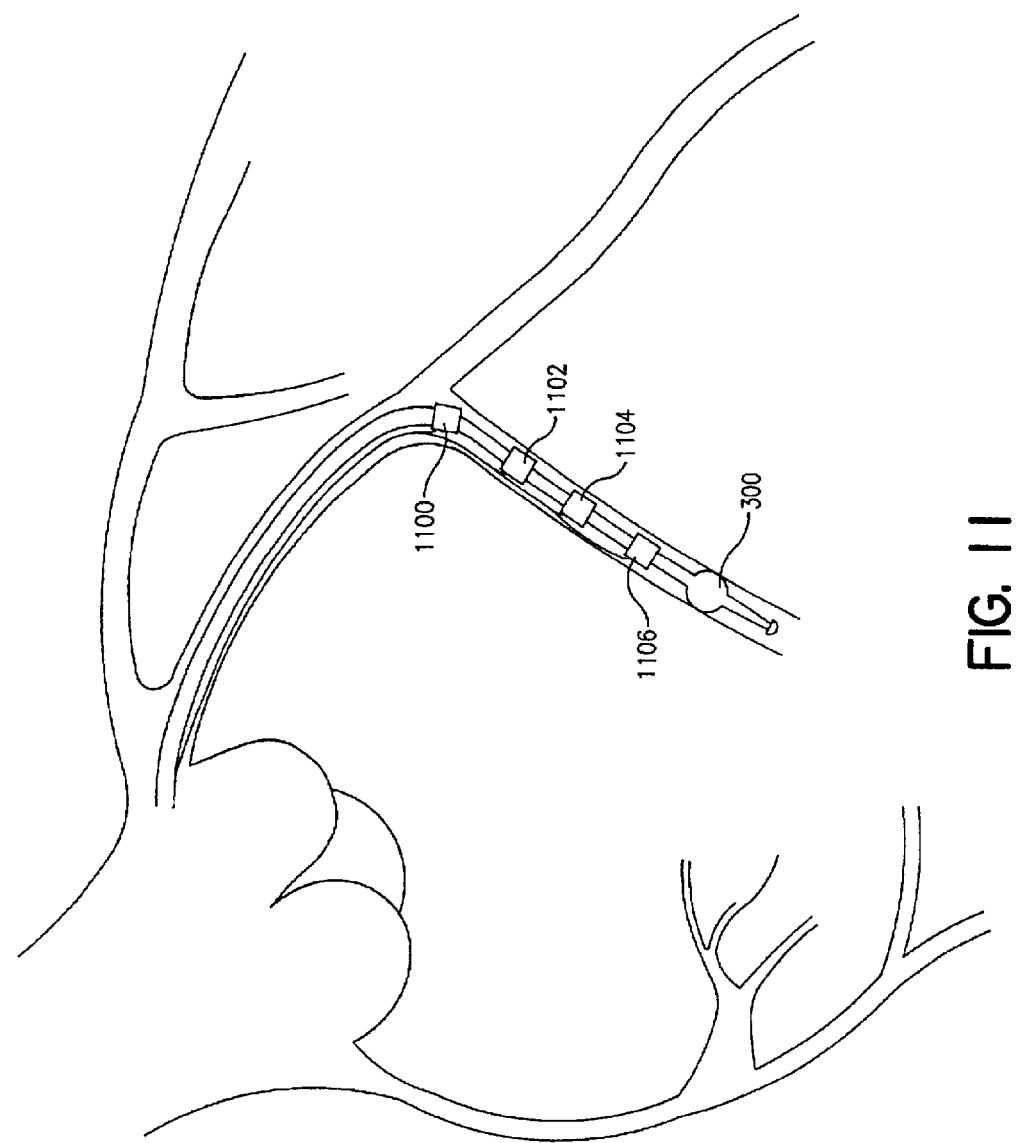
FIG. 11 is a plan view of the current inventive guidewire located within the vascular system of a human heart, with multiple electrode assemblies positioned over the guidewire at various implant sites.

FIG. 11 is a plan view of the current inventive guidewire located within the vascular system of a human heart, with electrode assemblies 1100–1106, which are of the type shown in FIG. 10, positioned along the lead body prior to electrode deployment.

FIG. 12A is a cross-sectional view illustrating another embodiment of the guidewire that includes a second lumen 72. The second lumen 72 may extend from the proximal end of guidewire 10 to a delivery port located distal to balloon 300. The second lumen is in fluid communication with an injection port at the proximal end of the guidewire that is adapted to receive a syringe. The second lumen may receive fluoro visible medium from the injection port, which in this instance is delivered to the delivery port distal to the balloon when the balloon is inflated. This allows a venogram to be taken during electrode deployment, and may aid in navigating the guidewire through the venous system. In another embodiment, the delivery port may be located proximal to the balloon to provide a view of the vascular system at the locations at which the electrodes will be deployed.

FIG. 12B is a cross-sectional view illustrating another embodiment of the guidewire of FIG. 12A. In this embodiment, the second lumen 72 is included within siderail 26. Therefore, in this embodiment, the delivery port will be located proximal to the balloon.

Figure 13:
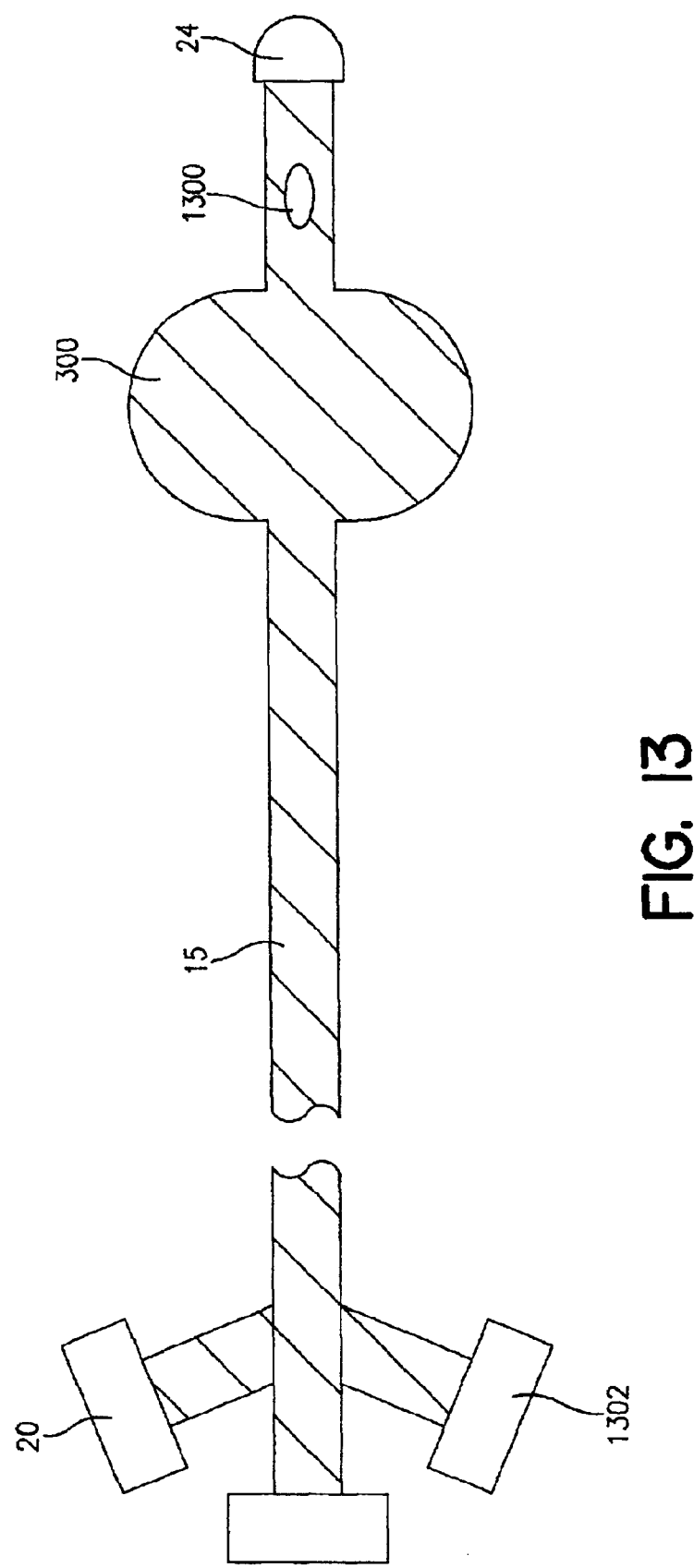
FIG. 13 is a top plan view of the guidewire similar to that of FIG. 12A including a delivery port for delivering fluoro visible media located distal to the balloon.

FIG. 13 is a top plan view of the guidewire similar to that of FIG. 12A showing delivery port 1300 distal to balloon 300 for infusing contrast medium into the body. As described above, contrast medium is injected via a syringe inserted into injection port 1302, which is in fluid communication with second lumen 72 (FIG. 12) and delivery port 1300.

The above described embodiments of guidewire 10 include an inflatable member to provide the means of fixing the guidewire at a desired implant site. This need not be the case. Other retractable fixation mechanisms may be used instead of the balloon for this purpose.

Figure 14A:
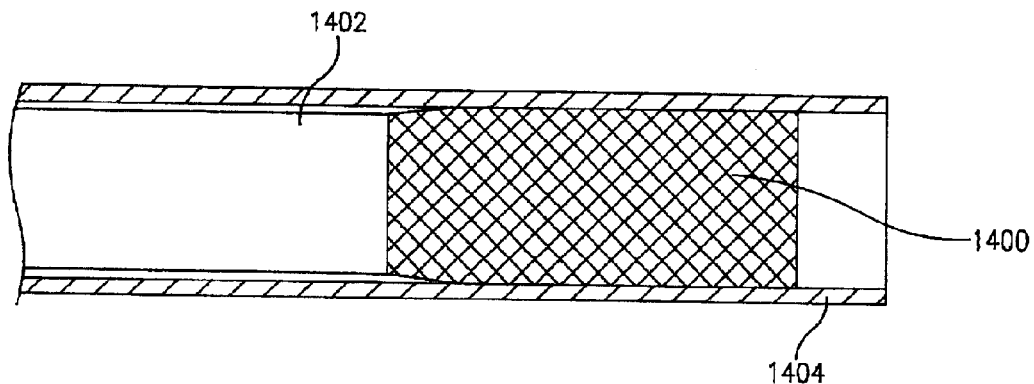
FIG. 14A is a side cutaway view of a self-expanding basket-like fixation member formed of braided flexible threads before the fixation member has been deployed in a body.

FIG. 14A is a side cutaway view of a self-expanding basket-like fixation member 1400 formed of braided flexible threads of a suitable implantable material. For example, fixation member 1400 may be formed of very fine, braided strands of a material such as Nitinol having superelastic properties. Alternatively a cobalt-chromium super alloy such as Elgiloy or MP35N may be used for the fixation member. The fixation member 1400 is attached via soldering, brazing, welding, or medical adhesive to the distal end of an inner tubular member 1402. This first tubular member is slidably disposed within an outer tubular member 1404.

Figure 14B:
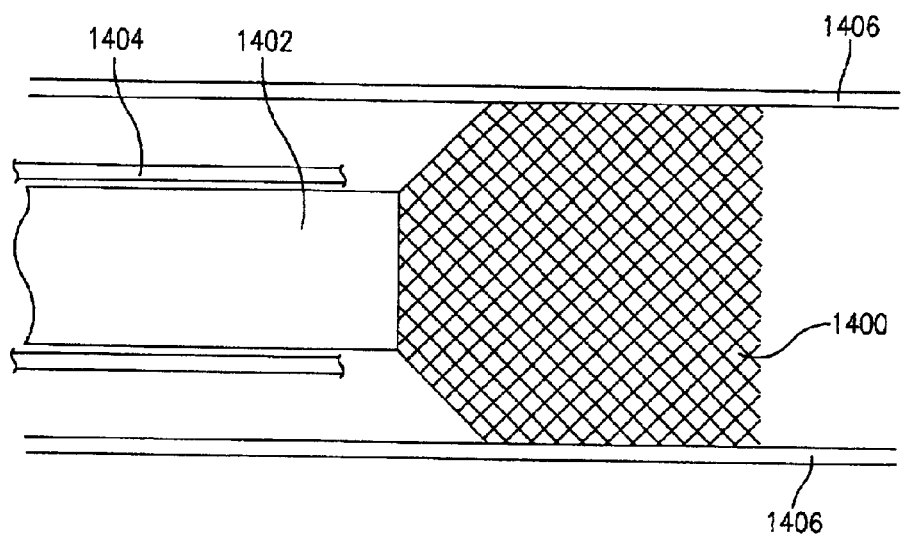
FIG. 14B is a plan view of the fixation member of FIG. 14A after the fixation member has been deployed.

FIG. 14B is a plan view of the fixation member 1400 of FIG. 14A after the fixation member has been deployed. This is accomplished by sliding the outer tubular member in a proximal direction, allowing the fixation member 1400 to expand and to make contact with the inner walls 1406 of a vessel.

Together, the inner and outer tubular members 1402 and 1404, respectively, of this embodiment comprise tubular member 15 of guidewire 10. Outer tubular member 1404 of this embodiment may therefore provide side rail 26 (FIG. 1), or alternatively, a channel for engaging a slidable side rail of the type shown in FIG. 7A. Any of the side rail embodiments discussed above may be incorporated into a design having this type of self-expanding fixation member.

Deployment of the self-expanding fixation member maintains the guidewire at a predetermined implant site during an implant procedure without total occlusion of the lumen. Following completion of the implant procedure, the fixation member may be reinserted within the outer tubular member 1404 by sliding the outer tubular member in a distal direction so that the configuration shown in FIG. 14A is again assumed.

In yet another embodiment, fixation member may assume the form of a radially expandable fixation member similar to any of the embodiments shown in U.S. Pat. Nos. 5,071,407 and 5,833,694 which are incorporated herein by reference in its entirety.

Other scopes and aspects of the current invention will become apparent from the description and figures included in Appendix A, which is incorporated herein by reference in its entirety.

What is claimed is:

1. A system for use in deploying one or more electrode assemblies, comprising:
    an elongated guiding device having a body extending from a proximal end to a distal end, deployable within a vascular structure;
    an expandable fixation member coupled to the distal end such that selective expansion of the fixation member secures the elongated guiding device within the vascular structure at a given position an electrode assembly; and
    a coupling member fixed on to the elongated guiding device body adapted to slidably engage an electrode assembly and having a terminal end such that advancement of the electrode assembly distal to the terminal end causes uncoupling of the electrode assembly from the coupling member within the vascular structure the coupling member and the fixation member being spaced apart along the guiding device body whereby the uncoupling of the electrode assembly is performed independently from the fixation member expansion, whereby the electrode assembly may be located at a predetermined site of implant while the fixation member is expanded.

2. The system of claim 1, wherein the coupling member is a rail member.

3. The system of claim 2, wherein the rail member is selected from the group consisting of a Y-rail, an H-rail, a K-rail, and a T-rail.

4. The system of claim 2, wherein the rail member includes a flexible extension adapted to allow each of the one or more electrode assemblies to more readily engage the rail member.

5. The system of claim 1, wherein the coupling member has means for preventing the electrode assembly from shifting laterally while sliding along the coupling member.

6. The system of claim 1, wherein the coupling member and the elongated guiding device are a unified structure.

7. The system of claim 1, wherein the expandable fixation member is an inflatable member.

8. The system of claim 1 or 7, wherein the elongated guiding device includes an infusion lumen and a delivery port in fluid communication with the infusion lumen whereby fluoro-visible medium may be injected to obtain a venogram.

9. The system of claim 8, wherein the infusion lumen is included in the coupling member.

10. The system of claim 8, wherein the delivery port is located proximal to the fixation member.

11. An implantable medical device, comprising:
    an elongated guiding device having a body extending from a proximal end to a distal end, deployable within a vascular structure;
    an expandable fixation member coupled to the distal end, such that selective expansion of the fixation member secures the elongated guiding device within the vascular structure at a given position;
    a fixed on to the elongated guiding device body and having a terminal end; and
    at least one electrode assembly adapted to sildably engage the coupling member, such that advancement of electrode assembly distal to the terminal end causes uncoupling of the electrode assembly from the coupling member the coupling member and the fixation member being spaced apart along the guiding device body whereby the uncoupling of the electrode assembly is performed independently from the fixation member expansion.

12. The system of claim 11, wherein the coupling member is a rail member.

13. The system of claim 12, wherein each of the at least one electrode assemblies includes a channel member to slidably engage the rail member.

14. The system of claim 13, wherein the rail member is selected from the group consisting of a Y-rall, an H-rail, a K-rail, and a T-rail.

15. The system of claim 11, wherein the coupling member has a rail for preventing each of the one or more electrode assemblies from twisting as the electrode assemblies slidably engage the coupling member.

16. The system of claim 11, wherein the coupling member and the elongated guiding device are a unified structure.

17. The system of claim 11, wherein the expandable fixation member is an inflatable member.

18. The system of claim 11, wherein predetermined ones of the at least one electrode assembly includes fixation means.

* * * * *

UNITED STATES PATENT AND TRADEMARK OFFICE
CERTIFICATE OF CORRECTION

| | |
|---|---|
| PATENT NO. | : 6,934,589 B2 |
| APPLICATION NO. | : 09/827108 |
| DATED | : August 23, 2005 |
| INVENTOR(S) | : Steve Sundquist et al. |

It is certified that error appears in the above-identified patent and that said Letters Patent is hereby corrected as shown below:

Column 14, line 49, delete "a Y-rall" and insert --a Y-rail--

Signed and Sealed this

Twenty-sixth Day of December, 2006

JON W. DUDAS
*Director of the United States Patent and Trademark Office*